US012679792B2

(12) United States Patent
Keller et al.

(10) Patent No.: US 12,679,792 B2
(45) Date of Patent: Jul. 14, 2026

(54) PROCESS FOR RECOVERING ISOPRENOL

(71) Applicant: BASF SE, Ludwigshafen am Rhein (DE)

(72) Inventors: Andreas Keller, Ludwigshafen am Rhein (DE); Hans Hasse, Kaiserslautern (DE); Rupert Wagner, Ludwigshafen am Rhein (DE); Bernhard Brunner, Ludwigshafen am Rhein (DE); Matthias Schult, Ludwigshafen am Rhein (DE); Stephan Maurer, Ludwigshafen am Rhein (DE); Heiko Hallmann, Ludwigshafen am Rhein (DE); Maximilian Dyga, Kaiserslautern (DE)

(73) Assignee: BASF SE, Ludwigshafen am Rhein (DE)

( * ) Notice: Subject to any disclaimer, the term of this patent is extended or adjusted under 35 U.S.C. 154(b) by 490 days.

(21) Appl. No.: 18/281,451

(22) PCT Filed: Mar. 11, 2022

(86) PCT No.: PCT/EP2022/056385
§ 371 (c)(1),
(2) Date: Sep. 11, 2023

(87) PCT Pub. No.: WO2022/189652
PCT Pub. Date: Sep. 15, 2022

(65) Prior Publication Data
US 2024/0158325 A1 May 16, 2024

(30) Foreign Application Priority Data
Mar. 12, 2021 (EP) ..................................... 21162449

(51) Int. Cl.
*C07C 29/80* (2006.01)
*B01D 3/14* (2006.01)
*C07C 33/025* (2006.01)

(52) U.S. Cl.
CPC .............. *C07C 29/80* (2013.01); *B01D 3/143* (2013.01); *C07C 33/025* (2013.01)

(58) Field of Classification Search
CPC ........ C07C 29/80; C07C 33/025; B01D 3/143
See application file for complete search history.

(56) References Cited

FOREIGN PATENT DOCUMENTS

DE 1279014 B 10/1968
DE 10064751 A1 6/2002
(Continued)

OTHER PUBLICATIONS

International Preliminary Report on Patentability received for PCT Patent Application No. PCT/EP2022/056385, mailed on Jan. 25, 2023, 6 pages.
(Continued)

*Primary Examiner* — Yate' K Cutliff
(74) *Attorney, Agent, or Firm* — Faegre Drinker Biddle & Reath LLP

(57) ABSTRACT

A process for recovering isoprenol essentially free of formaldehyde from a stream of crude isoprenol containing isoprenol, water and formaldehyde, the process comprising subjecting the stream of crude isoprenol or an isoprenol containing fraction thereof to distillation in a low-boiler separation tower operated at a pressure of 2.5 bara or higher to obtain a distillate stream containing aqueous formaldehyde and a bottoms stream containing isoprenol. The process of the invention allows for obtaining isoprenol essentially free of formaldehyde. Further provided is a plant for recovering isoprenol essentially free of formaldehyde from a stream of crude isoprenol containing isoprenol, water and
(Continued)

formaldehyde, the plant comprising a first low-boiler sepa-
ration tower, a second low-boiler separation tower, and a
finishing tower.

16 Claims, 7 Drawing Sheets

(56) References Cited

FOREIGN PATENT DOCUMENTS

| | | | |
|---|---|---|---|
| WO | 02/51776 | A2 | 7/2002 |
| WO | WO-2019030386 | A1 * | 2/2019 ............ C07C 29/80 |
| WO | 2020/049111 | A1 | 3/2020 |
| WO | 2020/187953 | A1 | 9/2020 |

OTHER PUBLICATIONS

International Search Report and Written Opinion received for PCT
Patent Application No. PCT/EP2022/056385, mailed on Jun. 15,
2022, 9 pages.
Bruycker et al., "Understanding the reactivity of unsaturated alco-
hols: Experimental and kinetic modeling study of the pyrolysis and
oxidation of 3-methyl-2-butenol and 3-methyl-3-butenol", Combus-
tion and Flame, vol. 171, No. 1, 2016, pp. 237-251.
Sekerova et al., "Prins cyclization of isoprenol with various alde-
hydes using MoO3/SiO2 as a catalyst", Reac Kinet Mech Cat, vol.
121, No. 1, 2017, pp. 83-95.

* cited by examiner (■) 293.15 K, (●) 313.15 K, (▲) 333.15
(□) 373.15 K, (○) 393.15 K. (——) model

PROCESS FOR RECOVERING ISOPRENOL

CROSS-REFERENCE TO RELATED APPLICATIONS

This application is a National stage application (under 35 U.S.C. § 371) of PCT/EP2022/056385, filed Mar. 11, 2022, which claims benefit of European Application No. 21162449.9, filed Mar. 12, 2021, both of which are incorporated herein by reference in their entirety.

The present invention relates to a process for recovering isoprenol essentially free of formaldehyde from a stream of crude isoprenol containing isoprenol, water and formaldehyde, and to a plant for recovering isoprenol.

Isoprenol, or 3-methyl-3-buten-1-ol (MBE), is an important intermediate for aroma compounds, such as citral, and vitamins, with a yearly global production of several thousand tons. Isoprenol is commercially synthesized by reacting formaldehyde with isobutylene (2-methylpropene). The process is described, e.g., in DE 100 64 751 A1. The reaction is typically carried out in the absence of solvents and at high pressures and high temperatures, as described in, e.g., WO 2020/049111 A1. DE 1 279 014 B describes a process for the production of alk-3-en-1-ols at high pressures and high temperatures performed in the presence of a base. WO 2019/030386 A1 relates to a process for recovering isoprenol from a feed stream comprising isoprenol, one or more solvents, water and isobutene via a series of distillation steps.

The reaction of formaldehyde with isobutylene is an equilibrium reaction and hence incomplete. Unreacted formaldehyde is predominantly isolated during downstream distillation steps and disposed of via accumulated wastewater. However, the known processes suffer from limited formaldehyde separation efficiency, so that formaldehyde tends to be ubiquitous in the distillation train and significant amounts are found in the isolated isoprenol. Contamination with formaldehyde may impair downstream processes and result in higher consumption rates, quality issues and challenging operability in production plants.

It is therefore an object of the present invention to provide a process for the recovery of isoprenol free of formaldehyde from a stream of crude isoprenol.

In a first aspect, the present invention provides a process for recovering isoprenol essentially free of formaldehyde from a stream of crude isoprenol containing isoprenol, water and formaldehyde, the process comprising subjecting the stream of crude isoprenol or an isoprenol containing fraction thereof to distillation in a low-boiler separation tower operated at a pressure of 2.5 bara or higher to obtain a distillate stream containing aqueous formaldehyde and a bottoms stream containing isoprenol.

In one embodiment, the isoprenol containing fraction of the crude isoprenol is crude isoprenol from which an amount of water and low-boilers have been separated in a first low-boiler separation tower. Doing so allows to obtain concentrated aqueous formaldehyde fit for recycle into the isoprenol synthesis, by distillation in a second low-boiler separation tower. Hence, in a second aspect the process comprises (i) directing the stream of crude isoprenol to a first low-boiler separation tower operated at a pressure of 1.5 bara or lower, to obtain a first bottoms stream containing isoprenol and formaldehyde, and a first distillate stream containing water and low-boilers;

(ii) directing the first bottoms stream to a second low-boiler separation tower operated at a pressure of 2 bara or higher, to obtain a second distillate stream containing aqueous formaldehyde, and a second bottoms stream containing isoprenol; and (iii) directing the second bottoms stream to a finishing tower to obtain pure isoprenol as a distillate stream, and a bottoms stream containing high-boilers.

Further provided is a plant for recovering isoprenol essentially free of formaldehyde from a stream of crude isoprenol containing isoprenol, water and formaldehyde, the plant comprising a first low-boiler separation tower, adapted to receive the stream of crude isoprenol and to distillatively separate the stream of crude isoprenol into a first bottoms stream containing isoprenol and formaldehyde, and a first distillate stream containing water and low-boilers;

a second low-boiler separation tower, adapted to receive a first bottoms stream from the first low-boiler separation tower and to distillatively separate the first bottoms stream into a second distillate stream containing aqueous formaldehyde, and a second bottoms stream containing isoprenol; and a finishing tower, adapted to receive a second bottoms stream from the second low-boiler separation tower and to distillatively separate the second bottoms stream into pure isoprenol as a distillate stream, and a bottoms stream containing high-boilers.

The selective recovery of formaldehyde from an aqueous alcoholic solution is extremely difficult. This difficulty arises from the fact that monomeric formaldehyde (as well as polymeric formaldehyde) forms both hydrates with water and hemiformals with alcohols such as isoprenol. The hydrates and hemiformals of varying formaldehyde polymerization degree have intermingling boiling points. The stability of and the equilibrium between hydrates and hemiformals is temperature-dependent. Formals formed in an upper region of a distillation tower may decompose in the hotter bottom of the tower, which adds additional complexity to the separation task.

It has, however, been found that formaldehyde can be separated virtually completely from isoprenol via distillation at a temperature at which the hemiformal is cleaved to formaldehyde and isoprenol, so that the formaldehyde can be easily separated from the isoprenol.

In particular, it has been found that the formaldehyde can be separated virtually completely from isoprenol and concentrated aqueous formaldehyde suitable for recycling into the isoprenol synthesis can be obtained in a distillation train involving a first distillation at a temperature at which the equilibrium is shifted towards the hemiformal of formaldehyde and isoprenol, so that essentially all formaldehyde remains in the bottoms of the distillation, and a second distillation at a temperature at which the hemiformal is cleaved to formaldehyde and isoprenol, so that the formaldehyde can be easily separated from the isoprenol.

These observations are illustrated by the appended ternary plots.

The following discussion focuses on the second aspect of the invention. It is understood that the operational parameters and description of embodiments and preferred embodiments relating to the "second low-boiler separation tower", "the second distillate stream containing aqueous formaldehyde", and "second bottoms stream containing isoprenol" according to the second aspect may also apply to the "low-boiler separation tower" "distillate stream containing aqueous formaldehyde", and "the bottoms stream containing isoprenol" according to the first aspect of the invention.

In order to permit a first distillation at a temperature below the isoprenol-formaldehyde dissociation temperature and a second distillation at a temperature above the isoprenol-formaldehyde dissociation temperature, the invention envisages two low-boiler separation towers operated at different pressures in the second aspect. Hence, at the relatively low pressure prevailing in the first low-boiler separation tower, a first distillate containing water and low-boilers essentially free of formaldehyde is obtained. At the relatively high pressure prevailing in the second low-boiler separation tower, a virtually all formaldehyde is separated from the isoprenol. The process of the invention thus allows for obtaining isoprenol essentially free of formaldehyde.

The term "essentially free of formaldehyde" is understood to indicate the absence of significant amounts of formaldehyde in the obtained pure isoprenol. Thus, the obtained pure isoprenol preferably comprises less than 0.5 wt.-%, more preferably less than 0.1 wt.-% of formaldehyde.

The crude isoprenol stream comprises isoprenol, water and formaldehyde. Preferably, the crude isoprenol stream comprises 50 to 75 wt.-% of isoprenol, more preferably 60 to 65 wt.-%. Preferably, the crude isoprenol stream comprises 15 to 40 wt.-% of water, more preferably 22 to 35 wt.-%. Preferably, the crude isoprenol stream comprises 1 to 5 wt.-% of formaldehyde, more preferably 2 to 3 wt.-%.

Preferably, the crude isoprenol stream is a liquid stream. The liquid stream can be a single-phase liquid stream or a two-phase liquid stream.

The crude isoprenol stream is generally the product stream of an isoprenol production process from which unreacted isobutylene has been removed. In an embodiment, the process comprises reacting formaldehyde with isobutylene to obtain a reaction mixture, and removing unreacted isobutylene from the reaction mixture in an isobutylene distillation tower to obtain the stream of crude isoprenol.

Formaldehyde is preferably reacted with isobutylene under supercritical conditions. Such conditions exist when a substance or mixture of substances is subjected to temperature and pressure exceeding the thermodynamic critical point of the substance or mixture. It has been found that under supercritical conditions the reactivity of isobutylene towards formaldehyde is sufficiently high to allow for high conversion at high selectivity.

In order to achieve supercritical conditions, formaldehyde and isobutylene are preferably reacted at a temperature of at least 220° C., for example in the range of 220 to 290° C., and an absolute pressure of at least 200 bar. All pressures cited herein are absolute pressures, unless noted otherwise. Further details regarding the reaction of formaldehyde with isobutylene under supercritical conditions may be found in WO 2020/049111 A1.

In a further embodiment, formaldehyde is reacted with isobutylene in the presence of a solvent and a heterogeneous catalyst.

The process according to the invention has the advantage that the second distillate is fit for recycling to the reaction of formaldehyde.

Unreacted isobutylene is removed from the reaction mixture in an isobutylene distillation tower, to obtain the stream of crude isoprenol.

Isobutylene is obtained as an isobutylene distillate stream. The isobutylene distillate stream preferably comprises at least 70 wt.-% of isobutylene, more preferably at least 85 wt.-%. The isobutylene distillate stream is preferably recycled to the reaction of formaldehyde with isobutylene.

Crude isoprenol is obtained as a bottoms stream from the isobutylene distillation column.

In order to minimize compression duty for the recycled isobutylene, the isobutylene distillation tower is suitably operated at a pressure of 4 to 15 bara, preferably 7 to 13 bara. All pressures of the towers and columns described herein are understood to relate to the absolute pressure at the top of the tower or column, unless mentioned otherwise. The isobutylene distillation tower may have from 5 to 40 theoretical plates, more preferably from 15 to 25 theoretical plates.

The bottoms temperature of the isobutylene distillation tower is generally in the range of 140 to 200° C., more preferably 160 to 180° C. The temperature at the top of the isobutylene distillation tower is preferably in the range of 50 to 90° C., more preferably 60 to 80° C.

In a particularly preferred embodiment, the isobutylene distillation tower is operated at a pressure in the range of 7 to 13 bara, a bottoms temperature in the range of 160 to 180° C. and a temperature at the top in the range of 60 to 80° C.

Under the conditions discussed above, the crude isoprenol stream obtained in the isobutylene distillation tower is in a superheated state. It is preferable that the crude isoprenol stream is directed to a decompression vessel prior to being directed to the first low-boiler separation vessel. In the decompression vessel, the crude isoprenol stream is decompressed, preferably to the pressure of the first low-boiler separation tower. In the decompression vessel, a vapor phase and a liquid phase are obtained, which are preferably directed to the first low-boiler separation tower via separate lines.

According to the second aspect of the invention, the crude isoprenol is directed to a first low-boiler separation tower operated at a pressure of 1.5 bara or lower. Any higher pressure of the crude isoprenol stream is preferably released before the same is directed to the first low-boiler separation tower. The crude isoprenol stream is preferably fed to the first low-boiler separation tower as a side stream, defining a rectifying section above the location of the feed and a stripping section below the location of the feed.

In the first low-boiler separation tower, a first bottoms stream containing isoprenol and formaldehyde, and a first distillate stream containing water and low-boilers are obtained. The term "low-boilers" is understood to refer to organic compounds (other than formaldehyde) having a boiling point lower than that of isoprenol, hence a boiling point of lower than about 130° C., at atmospheric pressure. The most common low-boilers are methanol and/or isoprenyl formate formed as by-products during the process.

In a preferred embodiment, the first low-boiler separation tower is operated at a pressure of 1.2 bara or lower, preferably 0.5 bara or lower. The bottoms temperature of the first low-boiler separation tower is preferably in the range of 80 to 135° C., more preferably 90 to 115° C., most preferably 95 to 105° C. The temperature at the top of the first low-boiler separation tower is preferably in the range of 45 to 105° C., more preferably 55 to 80° C.

In a particularly preferred embodiment, the first low-boiler separation tower is operated at a pressure in the range of 0.2 to 0.5 bara, a bottoms temperature in the range of 90 to 115° C. and a temperature at the top in the range of 55 to 80° C.

The first low-boiler separation tower preferably has from 15 to 65 theoretical plates, more preferably from 25 to 40 theoretical plates. In particular, the stripping section of the first low-boiler separation tower preferably has 10 to 25 theoretical plates. The rectifying section of the first low-boiler separation tower preferably has 5 to 40 theoretical plates.

The first bottoms stream preferably comprises 75 to 95 wt.-% of isoprenol, more preferably 80 to 90 wt.-%.

The first distillate is typically withdrawn at the top of the first low-boiler separation tower in gaseous form and condensed to obtain a liquid two-phase stream. The two-phase stream is preferably allowed to phase-separate in a separating vessel to obtain an aqueous phase and an organic phase. The aqueous phase is preferably passed to a wastewater stripping column described below. The organic phase is preferably partially returned to the top of the first low-boiler separation tower as a reflux stream. Another part of the organic phase is preferably discarded from the process to avoid the accumulation of water-insoluble low-boilers in the first low-boiler separation tower.

In a preferred embodiment, at least part of the first distillate stream is directed to a wastewater stripping column to separate low-boilers and entrained isoprenol from water. Preferably, the part of the first distillate stream directed to the wastewater stripping column is an aqueous phase obtained by condensation and phase separation of the first distillate stream, as discussed above.

In the wastewater stripping column, low-boilers are obtained as the low-boiler distillate stream, and wastewater is obtained as a bottoms stream. Both the low-boiler distillate stream and the wastewater bottoms stream are removed from the process, and each stream may be directed to further processing.

Moreover, isoprenol is preferably obtained as a side stream in the wastewater stripping column. The isoprenol side stream is typically a two-phase stream and preferably comprises 15 to 40 wt.-% of isoprenol, more preferably 25 to 35 wt.-%. The isoprenol side stream is preferably recycled to the first low-boiler separation tower.

The low-boiler distillate stream preferably comprises 75 to 95 wt.-% of low-boilers, more preferably 80 to 85 wt.-%.

The wastewater bottoms stream preferably comprises less than 1.2 wt.-% of organic matter, more preferably less than 0.6 wt.-%. The wastewater bottoms stream typically comprises formaldehyde in a concentration of 0.05 to 1.5 wt.-% of formaldehyde, such as 0.3 to 0.9 wt.-%.

The wastewater stripping column is preferably operated at a pressure of 1.5 bara or lower, preferably 1.1 bara or lower. The bottoms temperature of the wastewater stripping column is preferably in the range of 95 to 110° C., more preferably 97 to 103° C. The temperature at the top of the wastewater stripping column is preferably in the range of 65 to 100° C., more preferably 75 to 85° C.

In a particularly preferred embodiment, the wastewater stripping column is operated at a pressure in the range of 0.95 to 1.1 bara, a bottoms temperature in the range of 97 to 103° C. and a temperature at the top in the range of 75 to 85° C.

The wastewater stripping column preferably has from 6 to 30 theoretical plates, more preferably from 10 to 20 theoretical plates.

According to the second aspect, the first bottoms stream obtained in the first low-boiler separation tower is directed to a second low-boiler separation tower operated at a pressure of 2 bara or higher, preferably 2.5 bara or higher. The first bottoms stream is preferably fed to the second low-boiler separation tower as a side stream, defining a rectifying section above the location of the feed and a stripping section below the location of the feed.

In the second low-boiler separation tower, a second distillate stream containing or consisting essentially of aqueous formaldehyde, and a second bottoms stream containing isoprenol are obtained. The second bottom streams further comprises high-boilers. The term "high-boilers" is understood to refer to organic compounds having a boiling point higher than that of isoprenol, i.e. higher than about 130° C., at atmospheric pressure. Most common high-boilers are diols and/or oligomers formed as by-products during the process.

In a preferred embodiment, the second low-boiler separation tower is operated at a pressure of 2.5 bara or higher, preferably 2.8 bara or higher, most preferably 2.9 bara or higher. The bottoms temperature of the second low-boiler separation tower is preferably in the range of 160 to 200° C., more preferably 170 to 185° C., most preferably 175 to 180° C. The temperature at the top of the second low-boiler separation tower is preferably in the range of 115 to 160° C., more preferably 125 to 145° C.

In a particularly preferred embodiment, the second low-boiler separation tower is operated at a pressure in the range of 2.9 to 3.5 bara, a bottoms temperature in the range of 175 to 180° C. and a temperature at the top in the range of 130 to 140° C.

The second low-boiler separation tower preferably has from 20 to 60, more preferably from 35 to 60 theoretical plates. In particular, the stripping section of the first low-boiler separation tower preferably has 25 to 45 theoretical plates. The rectifying section of the first low-boiler separation tower preferably has 7 to 20 theoretical plates.

At the top of the second low-boiler separation tower, an offgas is typically obtained. The offgas primarily comprises nitrogen and may comprise traces of isoprenol, formic acid, water, formaldehyde and/or decomposition gases.

The second bottoms stream preferably comprises 82 to 96 wt.-% of isoprenol, more preferably 87 to 91 wt.-%. The relatively high pressure of the second low-boiler separation tower allows for a high degree of separation of formaldehyde and isoprenol. Thus, the second bottoms stream preferably comprises at most 0.5 wt.-% of formaldehyde, more preferably at most 0.1 wt.-%.

The second distillate stream is an aqueous stream, which preferably comprises 25 to 60 wt.-% of formaldehyde, more preferably 40 to 50 wt.-%, in particular 45 to 50 wt.-%. The second distillate stream preferably comprises at most 15 wt.-% of isoprenol, more preferably at most 5 wt.-%.

Owing to the broad condensation curve of the vapor emerging at the top of the second low-boiler separation tower, it is advantageous to use a condenser with liquid recycling. The direct condensation in a quench with liquid circulation is particularly advantageous. Hence, in a preferred embodiment of the process, a quench section is provided downstream, in vapor flow direction, of the rectifying section of the second low-boiler separation tower. The term "vapor flow direction" relates to the direction of the flow of gaseous components in the separation tower, i.e. upwards, towards the top of the tower. The quench section is preferably provided within the second low-boiler separation tower above the rectifying section.

The direct condensation in a quench also mitigates fouling caused by various condensation and polymerization mechanisms of formaldehyde that may occur at spots of high local formaldehyde concentrations. To avoid the risk of fouling in the second low-boiler separation tower and downstream processes, in particular in the offgas of the second low-boiler separation tower, the concentration of formaldehyde in the second distillate is preferably no higher than 60 wt.-%, more preferably no higher than 55 wt.-% and in particular no higher than 50 wt.-%.

At the lower end of the quench section, an aqueous liquid is collected. When the quench section is provided within the second low-boiler separation tower, the aqueous liquid may be collected, e.g., at a collecting tray above the rectifying section and beneath the quench section.

The aqueous liquid is partially circulated into the quench section through a circulation line and partially withdrawn as the second distillate. Suitably, the part of the aqueous liquid circulated into the quench section is circulated into the top of the quench section. Circulation of the aqueous liquid is typically achieved by use of a pump. As noted above, the second distillate may optionally be at least partially recycled to a reaction of formaldehyde with isobutylene.

The circulation of a part of the aqueous liquid into the quench section allows for cooling of vapors rising through the quench section, and absorption of formaldehyde from the vapors into the aqueous liquid. Thus, formaldehyde is quenched from the vapors rising through the quench section.

Further, the aqueous liquid is partially returned to the rectifying section of the second low-boiler separation tower as a reflux stream. This may be accomplished by a reflux line, or aqueous liquid may be partially returned to the rectifying section as overflow from a collecting tray beneath the quench section.

The mass flow ratio of the reflux stream to the second distillate is preferably in the range of 2:1 to 10:1, more preferably in the range of 3:1 to 7:1.

In a preferred embodiment, the aqueous liquid is cooled before being circulated into the quench section. Preferably, the part of the aqueous liquid withdrawn as the second distillate is a partial stream of the cooled aqueous liquid.

The temperature of the aqueous liquid collected at the lower end of the quench section is preferably in the range of 80 to 140° C., more preferably 125 to 135° C. The temperature of the cooled aqueous liquid circulated into the quench section is preferably 10 to 80° C. below the temperature of the aqueous liquid collected at the lower end of the quench section. This allows for an energetically favorable process.

The hot aqueous liquid withdrawn at the lower end of the quench section lends itself to heat-integration. In a suitable embodiment, it is heat-exchanged with the stream of crude isoprenol flowing into the first low-boiler separation tower before being circulated into the quench section.

In one embodiment, a scrubbing section is provided downstream, in vapor flow direction, of the quench section and water is introduced at the top of the scrubbing section. Preferably, the scrubbing section is provided within the second low-boiler separation tower above the quench section. The scrubbing section allows for maintaining the formaldehyde concentration in the second distillate below the critical concentrations described above and thus to avoid paraformaldehyde deposition in, e.g., offgas lines.

The mass flow ratio of the water introduced at the top of the scrubbing section to the first bottoms stream obtained in the first low-boiler separation tower is typically in the range of 0.01:1 to 0.06:1 more preferably in the range of 0.015:1 to 0.03:1.

According to the second aspect, the second bottoms stream is directed to a finishing tower, in which pure isoprenol is obtained as a distillate stream. High-boilers are withdrawn via a bottoms stream. As the second bottoms stream comprises essentially no formaldehyde, the separation task of the finishing tower is significantly less complex than in cases where formaldehyde separation is less efficient in the low-boiler separation section.

The pure isoprenol distillate stream preferably at least 97.0 wt.-% of isoprenol, more preferably 98.0 wt.-%, such as 98.1 to 99.5 wt.-%. Preferably, the pure isoprenol distillate stream comprises less than 0.5 wt.-% of formaldehyde, such as less than 0.1 wt.-% or less than 0.01 wt.-%.

The high-boiler bottoms stream preferably comprises 90 to 99.9 wt.-% of high-boilers, more preferably 99 to 99.8 wt.-%. Preferably, the high-boiler bottoms stream comprises less than 0.2 wt.-% of formaldehyde, such as less than 0.05 wt.-% of formaldehyde.

In a preferred embodiment, the finishing tower is operated at a pressure of 0.5 bara or lower, preferably 0.25 bara or lower. The bottoms temperature of the first low-boiler separation tower is preferably in the range of 130 to 190° C., more preferably 150 to 170° C. The temperature at the top of the finishing tower is preferably in the range of 60 to 90° C., more preferably 65 to 85° C.

In a particularly preferred embodiment, the finishing tower is operated at a pressure in the range of 0.05 to 0.2 bara, a bottoms temperature in the range of 150 to 170° C. and a temperature at the top in the range of 65 to 85° C.

The finishing tower preferably has from 6 to 40 theoretical plates, more preferably from 10 to 20 theoretical plates.

The towers and columns used in the inventive process and plant may be conventional distillation columns. Suitable types of distillation columns include packed columns, such as columns with random packing or structured packing, plate columns (i.e., tray columns), and mixed columns comprising both packings and trays.

Suitable plate columns may comprise internals over which the liquid phase flows. Suitable internals include sieve trays, bubble cap trays, valve trays, tunnel trays and Thormann® trays, in particular bubble cap trays, valve trays tunnel trays and Thormann® trays.

Random packed columns may be filled with a variety of shaped bodies. Heat and mass transfer are improved by enlarging the surface area by means of shaped bodies, which usually have a size in the range of 25 to 80 mm. Suitable shaped bodies include Raschig rings (hollow cylinders), Lessing rings, Pall rings, Hiflow rings and Intalox saddles. The packing materials may be provided in the column in a regular or irregular manner (as bulk material, i.e. loosely filled). Suitable materials include glass, ceramics, metal and plastics.

Structured packings are an advancement of regular packings and have a regularly shaped structure. This allows for the reduction of gas flow pressure loss. Suitable types of structured packings include fabric and metal sheet packings.

The term "top" or "head" of the column refers to a region free of internals located above the topmost tray or above the topmost layer of packing. It is generally formed by a domed base (head, e.g., Klopper head or Korbbogen head), which forms the terminating element of the distillation column.

The term "bottom" or "sump" of the column refers to a region free of internals located below the lowest tray or lowest layer of packing.

The inventive process may be carried out continuously or batchwise. Preferably, the inventive process is carried out continuously.

The present invention furthermore relates to a plant for recovering isoprenol essentially free of formaldehyde from a stream of crude isoprenol containing isoprenol, water and formaldehyde, the plant comprising a first low-boiler separation tower, adapted to receive the stream of crude isoprenol and to distillatively separate the stream of crude isoprenol into a first bottoms stream containing isoprenol and formaldehyde, and a first distillate stream containing water and low-boilers;

a second low-boiler separation tower, adapted to receive a first bottoms stream from the first low-boiler separation tower and to distillatively separate the first bottoms stream into a second distillate stream containing aqueous formaldehyde, and a second bottoms stream containing isoprenol;

a finishing tower, adapted to receive a second bottoms stream from the second low-boiler separation tower and to distillatively separate the second bottoms stream into pure isoprenol as a distillate stream, and a bottoms stream containing high-boilers.

It is understood that the embodiments described for the process of the invention above also relate to the plant of the invention, where applicable.

In a preferred embodiment, the second low-boiler separation tower of the plant comprises a quench section above a rectifying section of the second low-boiler separation tower, wherein the second low-boiler separation tower is designed to collect a second distillate at the lower end of the quench section and to partially circulate the second distillate into the quench section through a circulation line; and a scrubbing section above the quench section and a water inlet at the top of the scrubbing section.

In a preferred embodiment, the second low-boiler separation tower of the plant comprises an indirect heat exchanger designed to heat-exchange the aqueous liquid with a coolant stream before the aqueous liquid is circulated into the quench section. A suitable coolant stream intrinsic to the process is, e.g., the stream of crude isoprenol directed into the first low-boiler separation tower.

Alternatively, bottoms liquid of the first low-boiler separation tower may be circulated through the indirect heat-exchanger. This reduces the heating duty of the evaporator of the first low-boiler separation tower.

In a preferred embodiment, the plant comprises an isobutylene distillation tower, adapted to receive a fluid reaction mixture, and adapted to conduct a liquid stream of crude isoprenol to the first low-boiler separation tower.

In a preferred embodiment, the plant comprises a reactor, adapted for a high-pressure reaction of formaldehyde with isobutylene to obtain the fluid reaction mixture, and adapted to conduct the fluid reaction mixture to the isobutylene distillation tower.

In a preferred embodiment, the plant comprises a wastewater stripping column, adapted to receive the first distillate stream from the first low-boiler separation tower.

Figure 1:
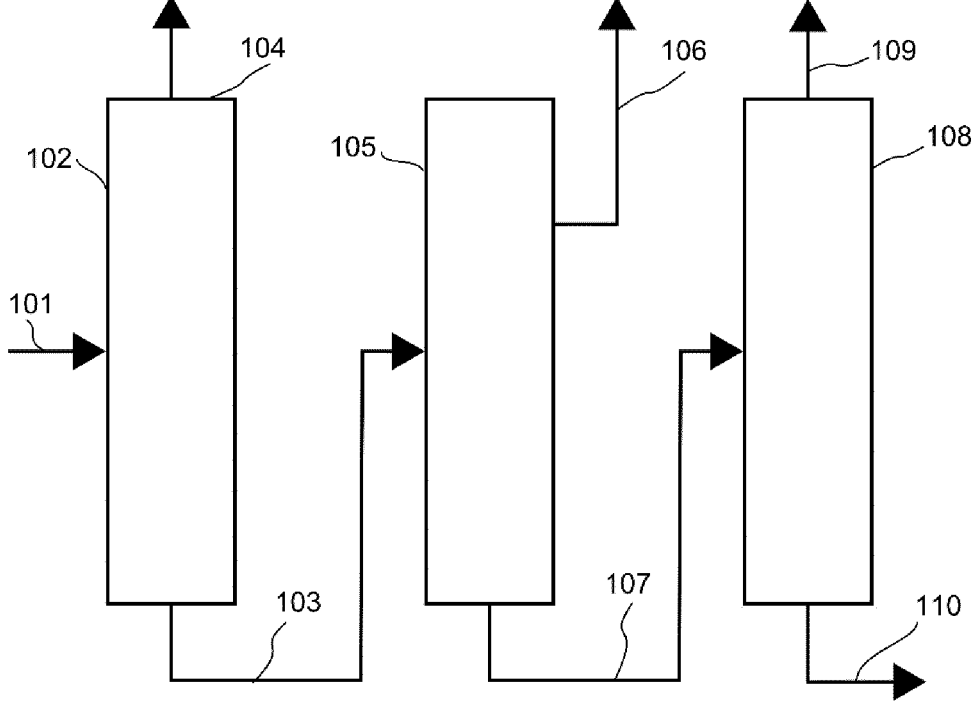
FIG. 1 schematically depicts a process for recovering isoprenol from a stream of crude isoprenol according to the invention in a plant according to the invention.

According to FIG. 1, a stream of crude isoprenol (101) containing isoprenol, water and formaldehyde is directed to a first low-boiler separation tower (102) operated at a pressure of 1.5 bara or lower. A first bottoms stream (103) containing isoprenol and formaldehyde, and a first distillate stream (104) containing water and low-boilers are obtained.

The first bottoms stream (103) is directed to a second low-boiler separation tower (105) operated at a pressure of 2 bara or higher. A second distillate stream (106) containing aqueous formaldehyde, and a second bottoms stream (107) containing isoprenol are obtained.

The second bottoms stream (107) is directed to a finishing tower (108). Pure isoprenol is obtained as a distillate stream (109). Moreover, a bottoms stream (110) containing high-boilers is obtained.

Figure 2:
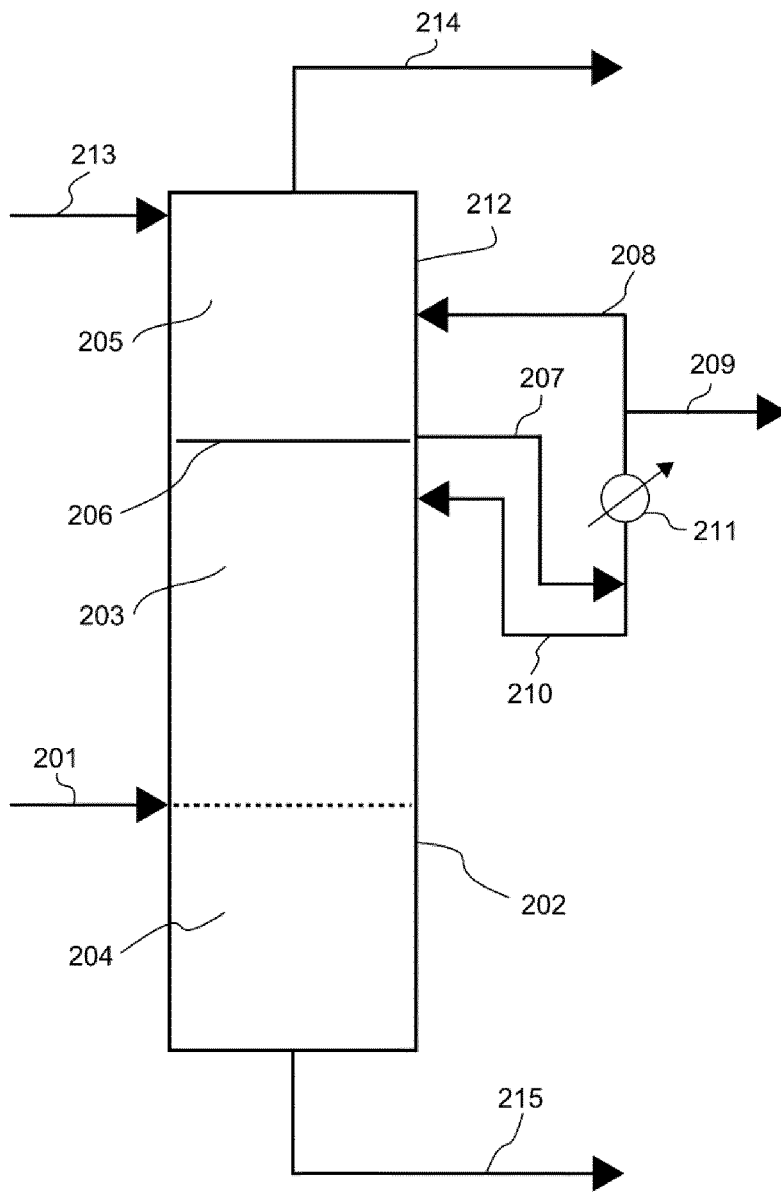
FIG. 2 schematically depicts a preferred embodiment of the second low-boiler separation tower used in the process according to the invention and present in the plant according to the invention.

According to FIG. 2, a first bottoms stream is directed via a line (201) to a second low-boiler separation tower (202) operated at a pressure of 2 bara or higher. The location of the feed of stream (201) defines a rectifying section (203) above the location of the feed and a stripping section (204) below the location of the feed, indicated by the dashed line.

A quench section (205) is provided downstream, in vapor flow direction, of the rectifying section of the second low-boiler separation tower (202), specifically within the second low-boiler separation tower above the rectifying section. A fitting (206), e.g., a plate, is located between the rectifying section (203) and the quench section (205).

An aqueous liquid is collected at the lower end of the quench section (205) via a line (207). The aqueous liquid is partially circulated into the top of the quench section (205) through a circulation line (208) and partially withdrawn as the second distillate via a line (209). Another part of the aqueous liquid is returned to the rectifying section as a reflux stream via a reflux line (210).

The part of the aqueous liquid circulated into the top of the quench section (205) is passed through a heat-exchanger (211), which is preferably adapted so that the aqueous liquid is heat-exchanged with the stream of crude isoprenol flowing into the first low-boiler separation tower (not shown in FIG. 2).

Further, a scrubbing section (212) is provided downstream, in vapor flow direction, of the quench section (205), and water is introduced at the top of the scrubbing section through a water inlet (213).

At the top of the second low-boiler separation tower (202), an offgas is removed via a gas line (214). At the bottom of the second low-boiler separation tower (202), a second bottoms stream is withdrawn via a line (215).

Figure 3:
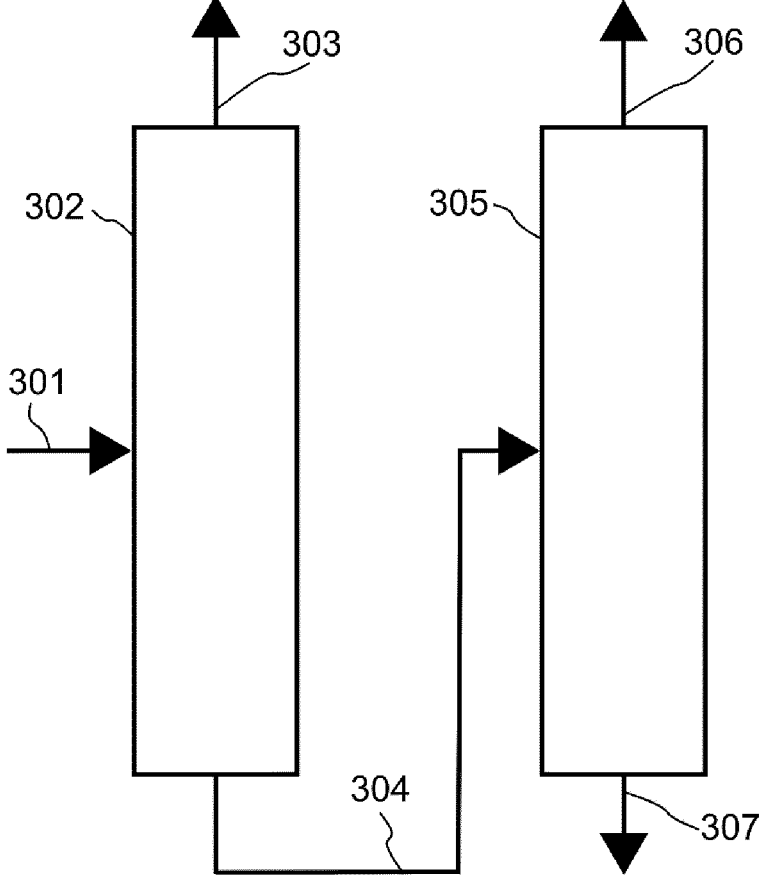
FIG. 3 schematically depicts a known process for recovering isoprenol from a stream of crude isoprenol.

According to FIG. 3, a stream of crude isoprenol (301) containing isoprenol, water and formaldehyde is directed to a low-boiler separation tower (302) operated at a pressure of 1.5 bara or lower. A distillate stream (304) containing water and low-boilers, and a bottoms stream (303) containing isoprenol and formaldehyde are obtained.

The bottoms stream (304) is directed to a finishing tower (305). Isoprenol is obtained as a distillate stream (306). Moreover, a bottoms stream (307) containing high-boilers is obtained.

Figure 4A:
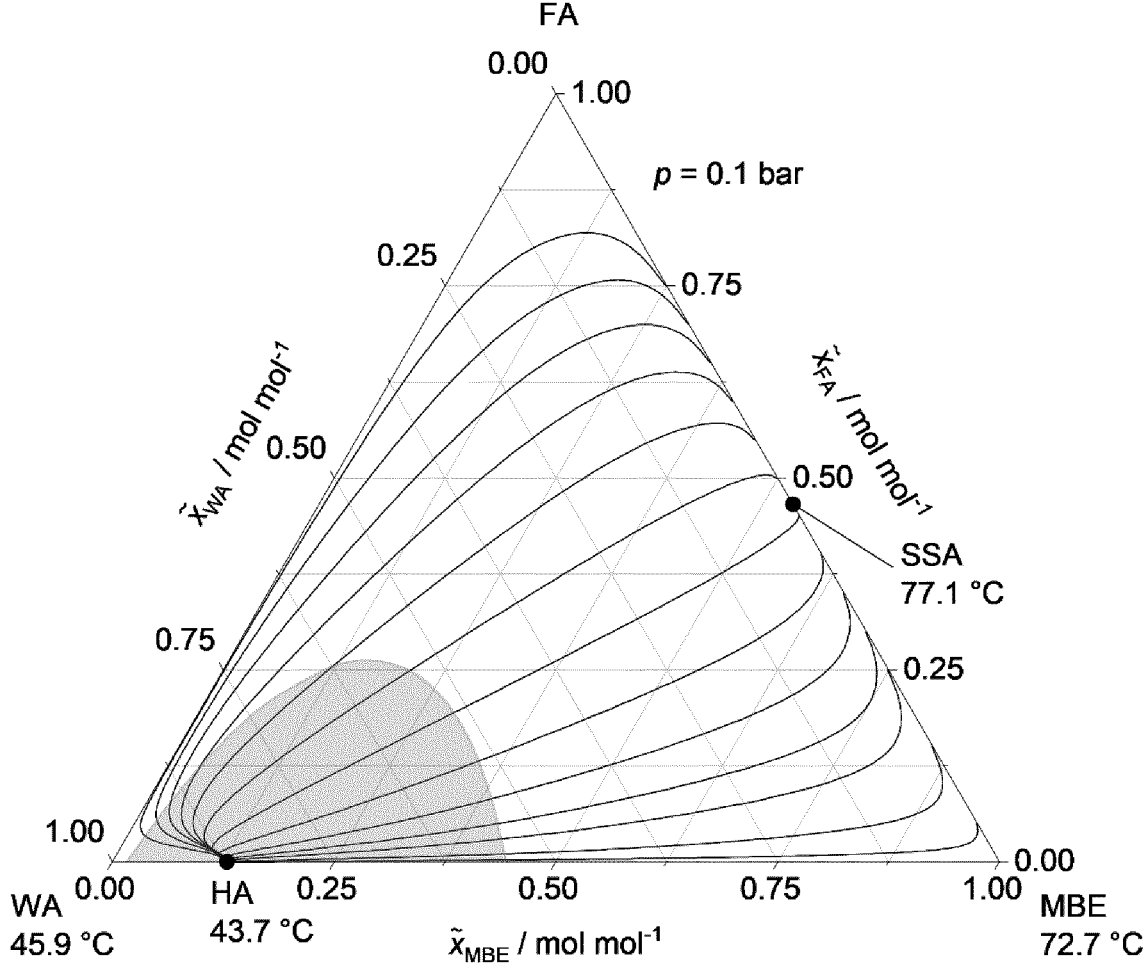
FIGS. 4a to 4c show ternary plots of mixtures of isoprenol, formaldehyde and water at different pressures.
Figure 4B:
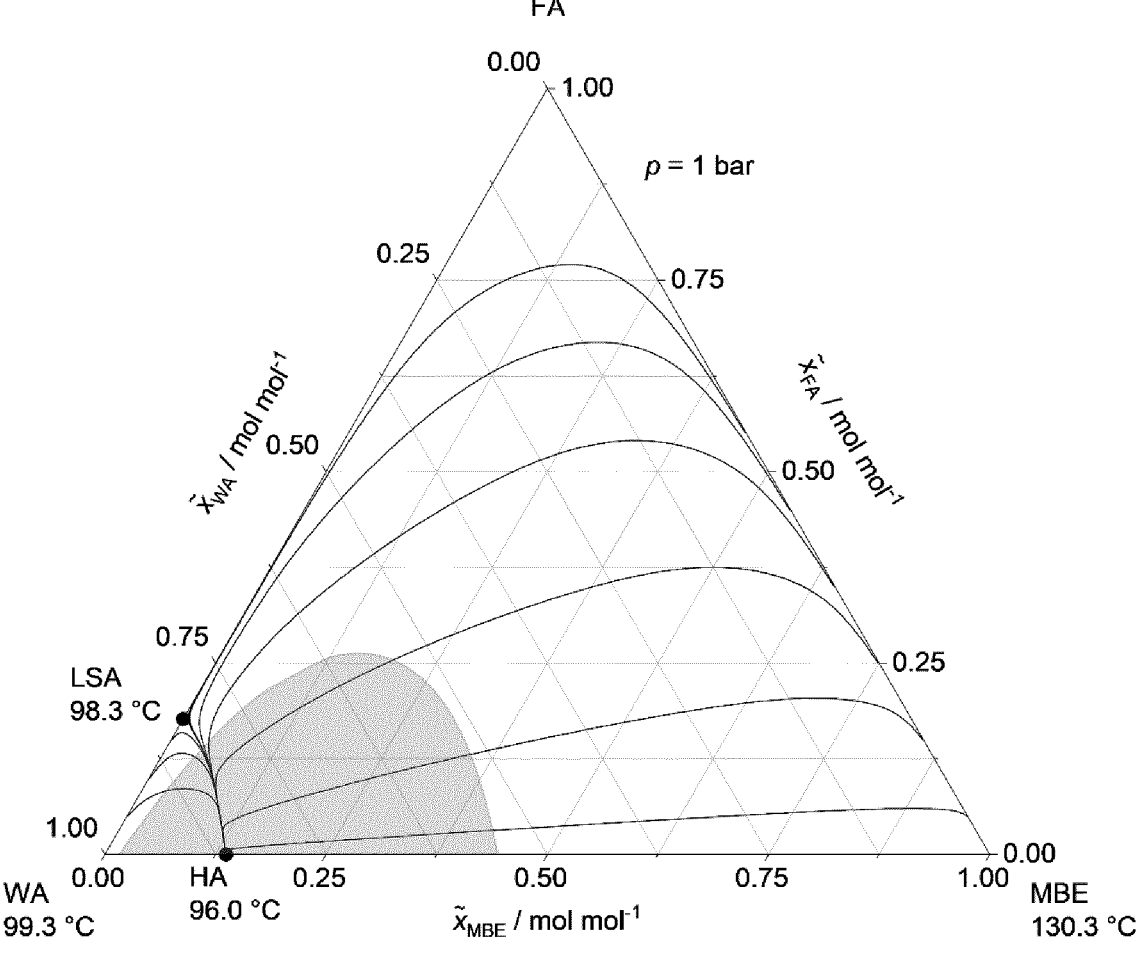
Figure 4C:
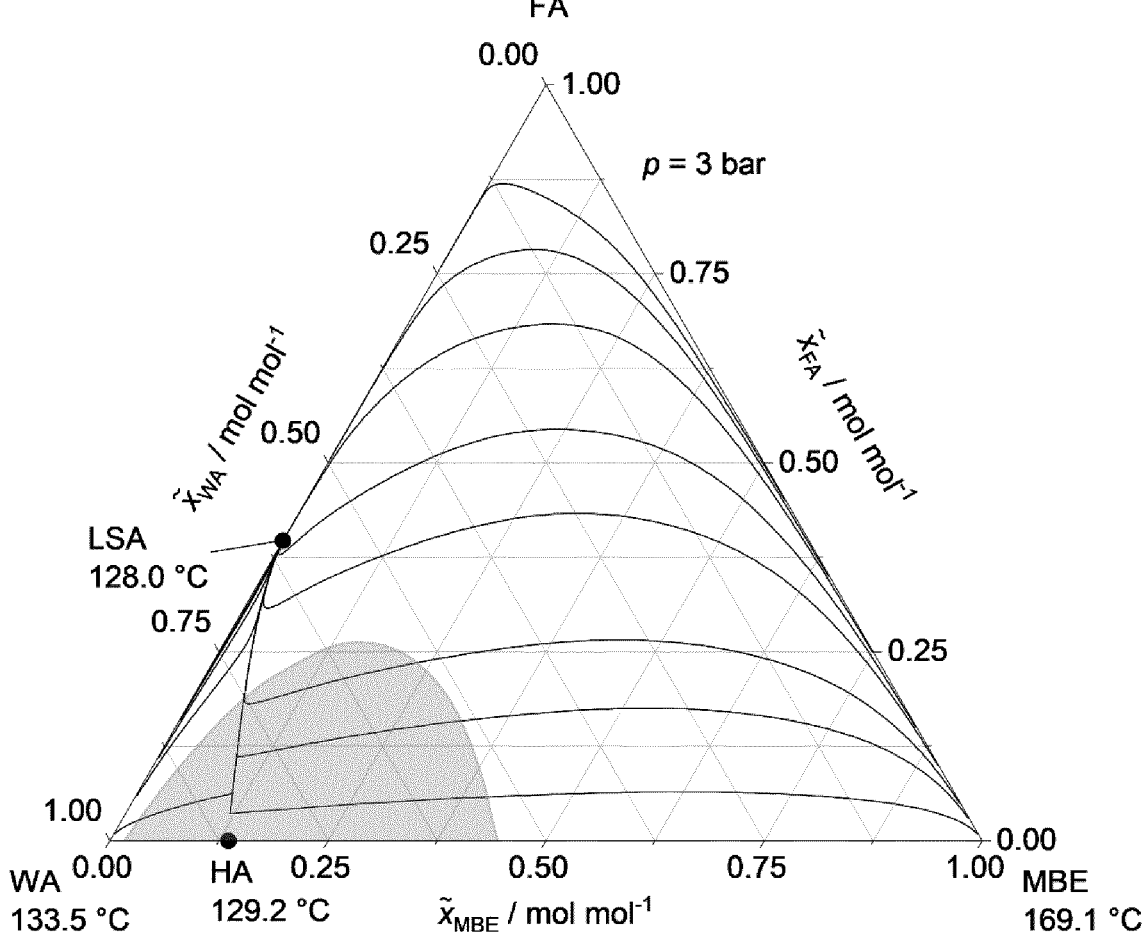

In FIGS. 4a to 4c, ternary plots of a mixture of isoprenol, formaldehyde and water at 0.1 bar (FIG. 4a), 1 bar (FIG. 4b) and 3 bar (FIG. 4c). Along the three sides, the ternary plots indicate the molar ratios of isoprenol, formaldehyde and water. For example, along the right-hand side, the molar ratio of formaldehyde to isoprenol (x FA) is indicated.

The curved lines are residue curves. Each residue curve represents a different feed composition with varying amounts of isoprenol, formaldehyde and water. The plot of the residue curves follows the liquid residue composition in a distillation column, i.e. from bottom (high temperature) to top (low temperature) of the column. In the shown ternary plots, i.e., following a residue curve to the higher temperature indicates the composition at the bottom of the column.

Following the residue curve to the lower temperature indicates the composition at the top of the column.

In the ternary plot of FIG. 4*a* (pressure of 0.1 bar), a water-isoprenol heteroazeotrope (HA) occurs, having a boiling point of 43.7° C. A high-boiling azeotrope (SSA) comprising isoprenol and all of the formaldehyde occurs, having a boiling point of 77.1° C.

In the ternary plot of FIG. 4*b* (pressure of 1 bar), the water-isoprenol heteroazeotrope (HA) has a boiling point of 96.0° C. Moreover, a water-formaldehyde low-boiling azeotrope (LSA) occurs (98.3° C.). A high-boiling azeotrope (SSA) of isoprenol and formaldehyde as observed in the ternary plot of FIG. 4*a* (0.1 bar) does not occur. Rather, isoprenol (130.3° C.) represents the high-boiling fraction.

In the ternary plot of FIG. 4*c* (pressure of 3 bar), the water-isoprenol heteroazeotrope (HA) has a boiling point of column so that the weight ratio of formaldehyde to water in the distillate was 1:1 (47.5 wt.-% of formaldehyde and 47.5 wt.-% of water). The isoprenol concentration in the distillate was 5 wt.-%.

The process was simulated via CHEMASIM (an open source version of which is available as OPEN CHEMASIM™; see H. Hasse, B. Bessling, R. Bottcher, OPEN CHEMASIM™: Breaking Paradigms in Process Simulation; Editor(s): W. Marquardt, C. Pantelides, Computer Aided Chemical Engineering, Elsevier, Volume 21, 2006, Pages 255-260, https://doi.org/10.1016/51570-7946(06) 80055-6).

The tower operation was simulated at varying pressures, and accordingly, varying bottom temperatures. The results are shown in the following table.

| | $\Delta p$ [bara] | H$_2$O fed to tower top [kg/h] | $\Delta T$ (bottom) [° C.] | FA conc. in bottoms [wt.-%] | Mass flow (distillate) [kg/h] | FA in bottoms [1] [%] | Yield [2] [%] |
|---|---|---|---|---|---|---|---|
| 3-1 * | 0.2 | 0.21 | 139.2 | 1.80 | 0.44 | 89.6 | 10.4 |
| 3-2 * | 0.3 | 0.37 | 141.6 | 1.64 | 0.78 | 81.4 | 18.6 |
| 3-3 * | 0.5 | 0.68 | 146.0 | 1.33 | 1.43 | 66.2 | 33.8 |
| 3-4 * | 1 | 1.35 | 155.9 | 0.66 | 2.85 | 32.3 | 67.7 |
| 3-5 * | 1.5 | 1.84 | 163.7 | 0.16 | 3.88 | 7.8 | 92.2 |
| 3-6 * | 2 | 1.99 | 170.7 | 0.016 | 4.18 | 0.8 | 99.2 |
| 3-7 | 3 | 2.00 | 182.6 | 0.0002 | 4.21 | 0.0 | 100.0 |

* Comparative Example
[1] FA in bottoms: proportion of formaldehyde in bottoms, relative to formaldehyde in feed
[2] Yield: proportion of formaldehyde in distillate, relative to formaldehyde in feed 129.2° C. The boiling point of the water-formaldehyde low-boiling azeotrope (LSA) is shifted to 128.0° C. and a higher formaldehyde concentration. At the bottom of the column, isoprenol is found essentially free of formaldehyde (169.1° C.).

Figure 5:
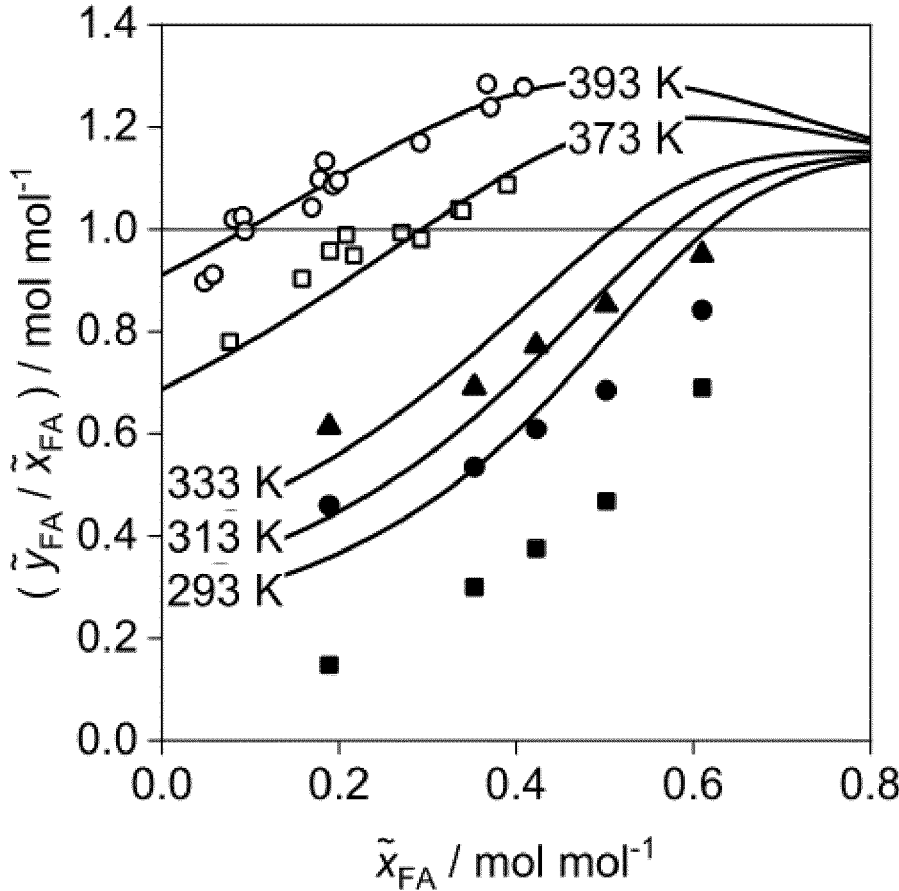
FIG. 5 shows the relative volatility of a mixture of isoprenol and formaldehyde at different temperatures.

FIG. 5 shows the relative volatility of formaldehyde in a mixture of isoprenol and formaldehyde fitted from experimental data. The term $\tilde{y}_{EA}$ indicates the mole fraction of formaldehyde in the gaseous phase. The term $x_{FA}$ indicates the mole fraction of formaldehyde (including the formaldehyde bounded as hemiformal) in the liquid phase. It is evident that the relative volatility of formaldehyde increases with higher temperatures, as indicated by the ratio of $\tilde{y}_{EA}$ to $x_{FA}$.

In particular, it can be seen that at 120° C. (393 K), the relative volatility ranges from 0.95 to slightly above 1.2. By reducing the temperature, the relative volatility is reduced, see the curves at 293 K, 313 K and 333 K. The higher the relative volatility of formaldehyde, the higher the degree of separation of formaldehyde as the low-boiling fraction from isoprenol.

EXAMPLES

Example 1

This example relates to the simulation of distillative formaldehyde removal from a liquid comprising 98 wt.-% of isoprenol and 2 wt.-% of formaldehyde (FA) in a low-boiler separation tower having 27 theoretical plates in the stripping section and 13 theoretical plates in the rectification section. The liquid was fed to the tower at 100 kg/h. At the top of the tower, a distillate comprising aqueous formaldehyde was obtained, 35 kg/h of which were returned to the top of the tower as a reflux stream. Water was added to the top of the It is evident that distillation at pressures above 2 bara allows for virtually complete FA removal and recovery of isoprenol at high purities.

Example 2 (Comparative)

In a process as depicted in FIG. 3, a stream of crude isoprenol (0.98 kg/h) containing isoprenol (66 wt.-%), water (22 wt.-%) and formaldehyde (1.7 wt.-%) was directed to a low-boiler separation tower. Further, an isoprenol recycle stream (0.02 kg/h) from a wastewater stripping column (not shown in FIG. 3), containing isoprenol, water and formaldehyde was directed to the low-boiler separation tower.

The low-boiler separation tower was operated at a pressure of 1 bara, a bottoms temperature of 130° C., and a top temperature of 97° C. A distillate stream (0.28 kg/h) containing water (83 wt.-%), isoprenol (7 wt.-%) and low-boilers (10 wt.-%), and a bottoms stream (0.72 kg/h) containing isoprenol (87 wt.-%), formaldehyde (2.4 wt.-%) and high-boilers (11 wt.-%) were obtained. The distillate stream was directed to the wastewater stripping column for further processing.

The bottoms stream was directed to a finishing tower operated at 0.1 bara, a bottoms temperature of 154° C., and a top temperature of 72° C. A bottoms stream (0.07 kg/h) containing more than 99.5 wt.-% high-boilers (diols and oligomers) was obtained.

The gaseous stream withdrawn from the top of the finishing tower was condensed in a condenser to obtain a condensate stream (1.60 kg/h). Part of the condensate (1.0 kg/h) was returned to the finishing tower as reflux. The remainder of the condensate (0.65 kg/h) was withdrawn as distillate. The distillate contained isoprenol and 2.7 wt.-% of formaldehyde.

In the wastewater stripping column, an isoprenol recycle stream was obtained as a side stream and was recycled to the low-boiler separation tower.

Example 3

In a process as depicted in FIG. 1, a stream of crude isoprenol (1.07 kg/h) containing isoprenol (67 wt.-%), water (19 wt.-%) and formaldehyde (1.9 wt.-%) was directed to a first low-boiler separation tower. Further, an isoprenol recycle stream from a wastewater stripping column (not shown in FIG. 1) was directed to the low-boiler separation tower. The process was simulated via CHEMASIM, as described with regard to Example 1.

The first low-boiler separation tower was operated at a pressure of 0.3 bara, a bottoms temperature of 103° C., and a top temperature of 67° C. A distillate stream (0.24 kg/h) containing water (86 wt.-%), isoprenol (12 wt.-%) and low-boilers (2 wt.-%), and a bottoms stream (0.85 kg/h) containing isoprenol (83 wt.-%), formaldehyde (2.3 wt.-%) and high-boilers (14.4 wt.-%) were obtained.

The first bottoms stream was directed to a second low-boiler separation tower as shown in FIG. 2, which was operated at a pressure of 3 bara, a bottoms temperature of 173° C., and a top temperature of 130° C. A quench section was provided above the rectifying section. A collecting tray was located between the rectifying section and the quench section. Further, a scrubbing section was provided above the quench section and water (0.02 kg/h) was introduced at the top of the scrubbing section through a water inlet.

An aqueous liquid (15 kg/h) was collected at the lower end of the quench section via the collecting tray. The aqueous liquid comprised formaldehyde (48 wt.-%), water (about 45 wt.-%) and isoprenol (about 7 wt.-%). The aqueous liquid was partially circulated into the top of the quench section through a circulation line (14.7 kg/h) and partially withdrawn as the second distillate (0.04 kg/h). Another part of the aqueous liquid was returned to the rectifying section as a reflux stream (0.23 kg/h) via a reflux line.

The aqueous liquid circulated into the top of the quench section was passed through a heat-exchanger. In the heat-exchanger, the aqueous liquid was heat-exchanged with the feed stream to the evaporator of the first low-boiler distillation tower. The aqueous liquid was cooled from 125° C. to 111° C.

At the top of the second low-boiler separation tower, an offgas (<0.01 kg/h) was removed via a gas line. At the bottom of the second low-boiler separation tower, a second bottoms stream (0.83 kg/h) containing isoprenol (85.2 wt.-%), water (less than 0.1 wt.-%), high-boilers (14.7 wt.-%) and formaldehyde (less than 0.1 wt.-%) was withdrawn.

The second bottoms stream was directed to a finishing tower operated at 0.1 bara, a bottoms temperature of 154° C., and a top temperature of 72° C. A bottoms stream (0.07 kg/h) containing high-boilers (comprising less than 0.4 wt.-% isoprenol) was obtained.

At the top of the finishing tower, a fluid stream (about 1.1 kg/h) was condensed in a condenser. The condensate contained isoprenol and less than 0.1 wt.-% of formaldehyde. Part of the condensate (about 0.4 kg/h) was returned to the finishing tower as reflux. The remainder of the condensate (0.72 kg/h) was withdrawn as second distillate. Apart from non-condensable components, no additional offgas stream for purging formaldehyde was necessary.

From the comparison of comparative example 2 and example 3, it is evident that the process of the invention allows for recovering isoprenol from a stream comprising isoprenol, water and formaldehyde.

The invention claimed is:

1. A process for recovering isoprenol essentially free of formaldehyde from a stream of crude isoprenol containing isoprenol, water and formaldehyde, the process comprising subjecting the stream of crude isoprenol or an isoprenol containing fraction thereof to distillation in a low-boiler separation tower operated at a pressure of 2.5 bara or higher to obtain a distillate stream containing aqueous formaldehyde and a bottoms stream containing isoprenol.

2. The process according to claim 1, comprising reacting formaldehyde with isobutylene to obtain a reaction mixture, and removing unreacted isobutylene from the reaction mixture in an isobutylene distillation tower to obtain the stream of crude isoprenol.

3. The process according to claim 2, wherein the second distillate is at least partially recycled to the reaction of formaldehyde with isobutylene.

4. The process according to claim 1, comprising
(i) directing the stream of crude isoprenol to a first low-boiler separation tower operated at a pressure of 1.5 bara or lower, to obtain a first bottoms stream containing isoprenol and formaldehyde, and a first distillate stream containing water and low-boilers;
(ii) directing the first bottoms stream to a second low-boiler separation tower operated at a pressure of 2.5 bara or higher, to obtain a second distillate stream containing aqueous formaldehyde, and a second bottoms stream containing isoprenol; and
(iii) directing the second bottoms stream to a finishing tower to obtain pure isoprenol as a distillate stream, and a bottoms stream containing high-boilers.

5. The process according to claim 4, wherein a quench section is provided downstream, in vapor flow direction, of a rectifying section of the second low-boiler separation tower, and an aqueous liquid is collected at the lower end of the quench section, wherein the aqueous liquid is partially circulated into the quench section through a circulation line and partially withdrawn as the second distillate.

6. The process according to claim 5, wherein the aqueous liquid is cooled before being circulated into the quench section.

7. The process according to claim 6, wherein the aqueous liquid is heat-exchanged with the stream of crude isoprenol flowing into the first low-boiler separation tower before being circulated into the quench section.

8. The process according to claim 5, wherein the aqueous liquid is partially returned to the rectifying section as a reflux stream.

9. The process according to claim 8, wherein the mass flow ratio of the reflux stream to the second distillate is in the range of 2:1 to 10:1.

10. The process according to claim 5, wherein a scrubbing section is provided downstream, in vapor flow direction, of the quench section and water is introduced at the top of the scrubbing section.

11. The process according to claim 4, wherein the second distillate comprises 25 to 60 wt.-%.

12. The process according to claim 4, wherein the obtained pure isoprenol comprises less than 0.5 wt.-%.

13. The process according to claim 4, wherein the first low-boiler separation tower is operated at a pressure of 1.2 bara or lower and/or wherein the second low-boiler separation tower is operated at a pressure of 2.5 bara or higher.

14. The process according to claim 4, comprising directing at least part of the first distillate stream to a wastewater stripping column to separate low-boilers from water.

15. A plant for recovering isoprenol essentially free of formaldehyde from a stream of crude isoprenol containing isoprenol, water and formaldehyde, the plant comprising a first low-boiler separation tower, adapted to receive the stream of crude isoprenol and to distillatively separate the stream of crude isoprenol into a first bottoms stream containing isoprenol and formaldehyde, and a first distillate stream containing water and low-boilers;

a second low-boiler separation tower, adapted to receive a first bottoms stream from the first low-boiler separation tower and to distillatively separate the first bottoms stream into a second distillate stream containing aqueous formaldehyde, and a second bottoms stream containing isoprenol; and a finishing tower, adapted to receive a second bottoms stream from the second low-boiler separation tower and to distillatively separate the second bottoms stream into pure isoprenol as a distillate stream, and a bottoms stream containing high-boilers.

16. The plant according to claim 15, wherein the second low-boiler separation tower comprises a quench section above a rectifying section of the second low-boiler separation tower, wherein the second low-boiler separation tower is designed to collect a second distillate at the lower end of the quench section and to partially circulate the second distillate into the quench section through a circulation line; and a scrubbing section above the quench section and a water inlet at the top of the scrubbing section.

\*  \*  \*  \*  \*